United States Patent
Alami et al.

(10) Patent No.: US 6,407,253 B1
(45) Date of Patent: Jun. 18, 2002

(54) METHOD FOR PREPARING 4-METHYL-BIPHENYL DERIVATIVES

(75) Inventors: Mouad Alami, Bussy Saint Georges; Gérard Cahiez, Paris; Bertrand Castro, Saint Aunes; Jean-Robert Dormoy, Sceaux; Eric Riguet, Les Ulis, all of (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 09/269,101
(22) PCT Filed: Sep. 17, 1997
(86) PCT No.: PCT/FR97/01648
§ 371 (c)(1),
(2), (4) Date: Jul. 14, 1999
(87) PCT Pub. No.: WO98/12174
PCT Pub. Date: Mar. 26, 1998

(30) Foreign Application Priority Data

Sep. 20, 1996 (FR) ............................................ 96/11514

(51) Int. Cl.[7] ...................... C07D 257/04; C07C 255/50
(52) U.S. Cl. ...................................... 548/250; 558/378
(58) Field of Search ......................... 558/378; 548/250

(56) References Cited

U.S. PATENT DOCUMENTS

| 5,128,355 A | 7/1992 | Carini et al. |
| 5,270,317 A | 12/1993 | Bernhart et al. |
| 5,288,895 A | 2/1994 | Bouisset et al. |

FOREIGN PATENT DOCUMENTS

| EP | 0 540 356 A2 | 5/1993 |
| WO | WO96/13489 | 5/1996 |

OTHER PUBLICATIONS

R.K. Russell and W.V. Murray, "Efficient Synthesis of 5–(4′–Methyl[1,1′–biphenyl]–2–yl)–1H–tetrazole", *J. Org. Chem.*, 1993, 58, 5023–5024.
Chem. Abst. 126: 7801r (1997); Derwent Abstract JP 8231454A.
Chem. Abst. 125: 86290d (1996); Derwent Abstract JP 8109143A.

*Primary Examiner*—Floyd D. Higel
*Assistant Examiner*—Ebenezer Sackey
(74) *Attorney, Agent, or Firm*—Michael D. Alexander; Paul E. Dupont

(57) ABSTRACT

The subject-matter of the invention is a process for the preparation of substituted 4-methylbiphenyls of general formula:

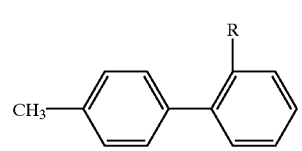

I in which R is a cyano group or a protected tetrazolyl group of formula:

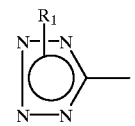

in which $R_1$, situated at the 1 or 2 position of the tetrazolyl group, is a protective group, characterized in that a halobenzene of formula:

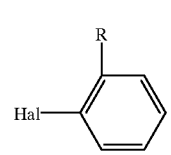

II in which Hal is a halogen atom and R has the same meaning as above, is reacted with a p-tolylmagnesium halide in the presence of a linear or branched polyether and of a catalyst comprising a transition metal.

17 Claims, No Drawings

METHOD FOR PREPARING 4-METHYL-BIPHENYL DERIVATIVES

This application is a 371 of PCT/FR 97/01648 filed on Sep. 17, 1997.

The present invention relates to a process for the preparation of substituted biphenyls. More particularly, the subject-matter of the invention is a process for the preparation of substituted 4-methylbiphenyls of general formula:

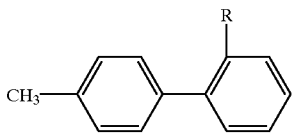

I in which R is a cyano group or a tetrazolyl group of formula:

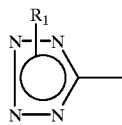

in which $R_1$, situated at the 1 position or preferably at the 2 position of the tetrazolyl group, is a protective group.

In particular, $R_1$ can be:
- a $(C_1-C_4)$ alkyl group
- a $(C_1-C_4)$ alkyl group monosubstituted or polysubstituted by an aryl group itself optionally monosubstituted or polysubstituted by a $(C_1-C_4)$ alkyl or $(C_1-C_4)$ alkoxy group
- a $(C_1-C_4)$ alkyl group substituted by (i) a $(C_1-C_4)$ alkoxy group or (ii) an aryloxy group optionally monosubstituted or polysubstituted by a $(C_1-C_4)$ alkyl or $(C_1-C_4)$ alkoxy group or else (iii) an arylalkyloxy group which is optionally monosubstituted or polysubstituted by a $(C_1-C_4)$ alkyl or $(C_1-C_4)$ alkoxy group and in which the alkyl part is $(C_1-C_4)$
- a $(C_1-C_4)$ alkyl group substituted by a $(C_1-C_4)$ alkylthio group
- a 2-tetrahydropyranyl, allyl or silyl group.

In the above formula I, "aryl" means, for example, phenyl or pyridyl, whereas "silyl" corresponds in particular to a silyl group trisubstituted by a $(C_1-C_4)$ alkyl group.

By way of examples, $R_1$ can be in particular a tert-butyl, benzyl, p-methoxybenzyl, 2-phenyl-2-propyl, diphenylmethyl, di(p-methoxyphenyl)methyl, trityl, (p-methoxyphenyl)diphenylmethyl, diphenyl(4-pyridyl)methyl, benzyloxymethyl, methoxymethyl, ethoxymethyl, methylthiomethyl, 2-tetrahydropyranyl, allyl, trimethylsilyl or triethylsilyl group.

The substituted 4-methylbiphenyls of formula I are known compounds which are particularly of use as intermediates in the synthesis of numerous medicinal active principles which act in particular against hypertension by a mechanism in which angiotensin II is inhibited.

Thus, the substituted tetrazolyls of formula I were disclosed in WO 96/13489, while the substituted cyano of formula I, that is to say o-(p-tolyl)benzonitrile, hereinafter denoted more briefly as ortho-tolylbenzonitrile or OTBN, was disclosed for the first time in EP 253,310.

A number of processes for the synthesis of OTBN have recently been provided. The process which seems to be the most appropriate is disclosed in EP 566,468 and consists of the reaction of an o-halobenzonitrile with a p-tolylmagnesium halide in the presence of a manganous salt, preferably $MnCl_2$, this reaction generally taking place in an ether, such as tetrahydrofuran, dibutyl ether or dioxane.

This method, with respect to those previously known, has the advantage of taking place in a single stage with yields of approximately 70% before crystallization. However, it gives 4,4-dimethylbiphenyl as a reaction byproduct resulting from the condensation of p-tolylmagnesium halide with itself.

Furthermore, results of orientation tests for the preparation of OTBN from p-tolylmagnesium bromide and 2-chlorobenzonitrile have been reported in EP 566,468 in question, the reaction being carried out in tetrahydrofuran in the presence or absence of various catalysts comprising a transition metal, namely $PdCl_2$, $NiCl_2$, or $Pd(PPh_3)_4$. These tests showed poor, even zero, yields of OTBN, depending on the methods used, such as yields varying from 0 to 27%.

It has now been found, surprisingly, that, when the coupling between the o-halobenzonitrile and the p-tolylmagnesium halide is carried out in the presence of a linear or branched polyether and of traces of a catalyst comprising a transition metal, OTBN is obtained with a yield of at least approximately 92%, while the 4,4'-dimethylbiphenyl impurity falls below approximately 3.5%.

Such results, however, could not be observed when the linear or branched polyether is completely replaced by a cyclic diether in which the two endocyclic oxygens form part of the same ring, in this case dioxane.

Thus, the subject-matter of the present invention is a process for the preparation of the compounds of formula I in general and of o-(p-tolyl)benzonitrile in particular, characterized in that a halobenzene of formula

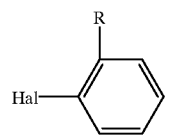

II in which Hal is a halogen atom, preferably bromine, and R has the same meaning as above, is reacted with a p-tolylmagnesium halide in the presence of a linear or branched polyether and of a catalyst comprising a transition metal.

Linear or branched polyether is understood to denote any organic compound comprising at least two ether functions forming part of a ring or of a linear or branched hydrocarbon chain, with the exception of compounds in which all the ether functions are endocyclic and form part of the same ring.

According to a preferred embodiment, the linear or branched polyether is a linear or branched diether, the two ether functions of which, when they are both endocyclic, do not form part of the same ring.

The linear or branched diether is advantageously such that its two ether functions are incorporated in a linear or branched, preferably $(C_2-C_{12})$, better still $(C_2-C_6)$, hydrocarbon chain.

The coupling reaction according to the invention is carried out in a medium composed of a linear or branched polyether, to which has optionally been added a solvent of the monoether type, such as methyl tert-butyl ether or dibutyl ether, or alternatively a cyclic mono- or diether, such as dioxane or tetrahydrofuran, it being possible for the reaction temperature to vary from −10 to 65° C. depending on the medium employed.

In fact, it has been found that, in order to improve the progress of the reaction in question, it is essential to carry out the reaction in the presence of a polyether of this type, generally a glycolic diether. According to the invention, a glycolic ether is a glycol ether in which the glycol is composed of a linear or branched, preferably ($C_2$–$C_{12}$), better still ($C_2$–$C_6$), dihydroxylated hydrocarbon chain. Ethers of 1,2-glycol and in particular diethylene glycol are more particularly advantageous.

In this respect, diethoxyethane and, preferably, dimethoxyethane have proved to be particularly advantageous.

This coupling reaction results in the transient formation of a complex, which is hydrolysed according to the usual procedures, for example by means of an acid, such as hydrochloric acid.

The transition metal forming the catalyst is advantageously cobalt, nickel, platinum, manganese or, in particular, palladium.

Use is preferably made, as catalyst comprising a transition metal, of a palladium(II) salt, in particular the nitrate, chloride, acetate, bromide, sulphate or the like, the chloride ($PdCl_2$) and the acetate ($CH_3$—COO—Pd—OOC—$CH_3$) being particularly advantageous. The palladium salt is preferably complexed, for example with at least one organophosphorus compound comprising trivalent phosphorus. More particularly, use is made of palladium complexes, such as bis(triphenylphosphine)dichloro-, bis(tributylphosphine) dichloro-, bis(tricycloheylphosphine) dichloro-, diallyltriphenylphosphinedichloro-, triphenylphosphinepiperidinodichloro-, bis (cyclohexyloxime)dicarbonyl-, 1,5,9-cyclododecatrienedichloro-, bis(triphenylphosphine) dicarbonyl-, bis(triphenylphosphine)diacetate-, bis (triphenylphosphine)sulphate- or (2,4-pentanedione), tetrakis(triphenylphosphine) palladium. Among these, palladium(II) complexes are particularly advantageous 1,3-bis(diphenylphosphino)propane (dppp) complex with palladium(II) chloride or palladium(II) acetate being preferred.

The palladium salts and the organophosphorus compounds can be added separately to the reaction mixture. In this case, the amount of organophosphorus compound is preferably sufficient to form the catalyst in situ in the form of a complex with the palladium present.

The said complex is generally prepared so that the P/Pd ratio is approximately 1/1 but such a ratio can vary between 0.5/1 and 2/1 without having a significant detrimental effect on the result of the process.

This catalyst is present in very small amounts in the reaction mixture, namely from 0.001 to 2 molar % per mole of starting o-halobenzonitrile.

According to a preferred procedure, the p-tolylmagnesium halide is in equimolar amounts or in slight excess (1 to 1.7 mol) with respect to the o-halobenzonitrile.

In addition, the reaction can be carried out in tetrahydrofuran comprising dimethoxyethane by adding, at a temperature of 10° C., the catalyst and the o-halobenzonitrile, optionally in solution in tetrahydrofuran, to a tetrahydrofuran solution comprising the p-tolylmagnesium halide. This reaction, which is exothermic, can be controlled by adjusting the rate of addition of the substituted benzonitrile and of the catalyst, so as to maintain it below 35° C.

Alternatively, the reaction can also be carried out by adding the p-tolylmagnesium halide in, for example, tetrahydrofuran to a mixture of o-halobenzonitrile and of catalyst in, for example, tetrahydrofuran comprising dimethoxyethane. In this case, the reaction temperature can be better controlled and the addition of p-tolylmagnesium halide can be carried out even at a high temperature, about 60–65° C., so as to decrease the duration of the reaction and the amount of catalyst employed.

According to the above preferred procedure, hydrolysis is carried out in situ with hydrochloric acid and the OTBN thus formed is isolated according to conventional techniques, for example by extraction with a suitable solvent, evaporation of the solvent and purification by crystallization from ethanol or by chromatography.

The OTBN is thus obtained with very high yields, from 92 to 98%, depending on the proportions of reactants employed. It comprises very small amounts of 4,4'-dimethylbiphenyl, generally less than 3.5%.

The amount of 4,4'-dimethylbiphenyl which is formed according to the process of the present invention has been compared with that which is formed according to the process disclosed in EP 566,468. Thus, by carrying out the preparation:

according to EP 566468, namely by using only $MnCl_2$ as catalyst, in a series of tests under the same conditions, the 4,4'-dimethylbiphenyl byproduct was obtained with a yield of 8 to 12% with respect to the tolylmagnesium bromide, i.e. 6.5 to 10% by weight of 2-(p-tolyl) benzonitrile final product;

according to the present invention, namely in the presence of dimethoxyethane and by using $PdCl_2$/dppp as catalyst, in a series of tests under the same conditions, the 4,4'-dimethylbiphenyl byproduct was obtained with a yield of 0.5 to 1% with respect to the p-tolylmagnesium bromide, i.e. at most 0.65% by weight of final product.

The catalyst comprising a transition metal can also be a cobalt, nickel, platinum or manganese salt, as indicated above.

In the case of a catalyst comprising nickel, use is generally made of a nickel(II) salt, such as nickel chloride or acetylacetonate. This salt is preferably complexed with at least one organophosphorus compound comprising trivalent phosphorus, such as a phosphine, for example triphenylphosphine. The nickel salt and the organophosphorus compound can be added separately to the reaction mixture.

This nickel-comprising catalyst is advantageously pretreated with a reducing agent, such as a hydride, for example dibutylaluminium hydride or diisobutylaluminium hydride, or alternatively with a methylmagnesium halide, for example methylmagnesium chloride, so as to form catalysts comprising Ni(O), such as $Ni[P(C_6H_5)_3]_4$.

Systems comprising nickel acetylacetonate, triphenylphosphine and diisobutylaluminium hydride have proved to be particularly advantageous.

As regards the manganese salt, generally a manganous salt, it is preferably $MnCl_2$ or $MnCl_4Li_2$, it being possible for the latter to be formed in situ by addition of two molar equivalents of LiCl and of one molar equivalent of $MnCl_2$.

These catalysts, formed by cobalt, nickel, platinum or manganese salts, can be employed in the process of the invention in a way similar to that described above for the palladium(II) salts.

As indicated above, the 4-methylbiphenyl derivatives of formula I can be used in the preparation of medicines which are antagonists of angiotensin II.

Methods for the preparation of these medicines starting from the compounds of formula I have been widely disclosed. In this respect, reference will be made, for example, to WO 96/13489, EP 253,310, EP 324,377 or EP 454,511.

The following non-limiting Example illustrates the invention. In this example, the molar percentages of catalyst are calculated with respect to the amount of ortho-halobenzonitrile.

EXAMPLE

Preparation of o-(p-tolyl)benzonitrile

Four molar equivalents of dimethoxyethane (approximately 2 ml), 1/1 $PdCl_2$/dppp (0.023 g, 1 mol %) and then o-bromobenzonitrile (0.72 g, 3.955 mol) are successively added, under a nitrogen atmosphere, to 7 ml of anhydrous tetrahydrofuran. The mixture is stirred for 5 minutes and is then heated to 65° C. A solution of p-tolylmagnesium chloride in tetrahydrofuran (1N, 6.73 ml, 6.73 mmol) is then added over 7 minutes.

After stirring for 5 minutes at 65° C., the reaction mixture is cooled to room temperature and is then hydrolysed using a 1N hydrochloric acid solution (15 ml). After extracting with ethyl ether, the organic phase is dried over potassium carbonate, filtered and then evaporated under vacuum. The oil obtained is purified by chromatography (silica: 20 g; eluent: 95/5 petroleum ether/ethyl acetate). o-(p-Tolyl) benzonitrile is thus obtained with a yield of 93% in the form of off-white crystals.

What is claimed is:

1. A process for the preparation of a substituted 4-methylbiphenyl of formula:

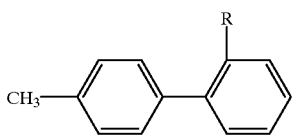

in which R is a cyano group or a protected tetrazolyl group of formula:

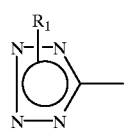

in which $R_1$, situated at the 1 or 2 position of the tetrazolyl group, is a protective group, the said process providing a reduction in the formation of the 4,4'-dimethylbiphenyl impurity, wherein a halobenzene of formula:

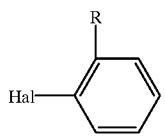

in which Hal is a halogen atom and R has the same meaning as above, is reacted with a p-tolylmagnesium halide in the presence of a glycolic diether and of a catalyst comprising a transition metal.

2. A process according to claim 1, wherein $R_1$ is selected from the group consisting of:

a $(C_1-C_4)$ alkyl group;

a $(C_1-C_4)$ alkyl group monosubstituted or polysubstituted by an aryl group itself optionally monosubstituted or polysubstituted by a $(C_1-C_4)$ alkyl or $(C_1-C_4)$ alkoxy groups;

a $(C_1-C_4)$ alkyl group substituted by a member selected from the group consisting of (i) a $(C_1-C_4)$ alkoxy group (ii) an aryloxy group optionally monosubstituted or polysubstituted by a $(C_1-C_4)$ alkyl or $(C_1-C_4)$ alkoxy group; and (iii) an arylalkyloxy group which is optionally monosubstituted or polysubstituted by a $(C_1-C_4)$ alkyl or $(C_1-C_4)$ alkoxy group and in which the alkyl part is $(C_1-C_4)$;

a $(C_1-C_4)$ alkyl group substituted by a $(C_1-C_4)$ alkylthio group; and a 2-tetrahydropyranyl, allyl or silyl group.

3. A process according to claim 1 wherein $R_1$ is selected from the group consisting of: tert-butyl, benzyl, p-methoxybenzyl, 2-phenyl-2-propyl, diphenylmethyl, di(p-methoxyphenyl)methyl, trityl, (p-methoxyphenyl) diphenylmethyl, diphenyl(4-pyridyl)-methyl, benzyloxymethyl, methoxymethyl, ethoxymethyl, methylthiomethyl, trimethylsilyl or triethylsilyl.

4. A process according to claim 1 wherein Hal is bromine.

5. A process according to claim 1 wherein the catalyst comprising a transition metal is selected from the group consisting of a palladium salt, a cobalt salt, a nickel salt, a platinum salt and a manganese salt.

6. A claim 1 wherein the catalyst comprising a transition metal is a palladium(II) salt.

7. A process according to claim 6, wherein the palladium (II) salt is palladium(II) chloride or palladium(II) acetate.

8. A process according to claim 5 wherein the palladium salt is added to the reaction mixture with an organophosphorus compound comprising trivalent phosphorus.

9. A process according to claim 5 wherein the palladium salt is in the form of a complex with an organophosphorus compound comprising trivalent phosphorus.

10. A process according to claim 9, wherein the palladium salt is in the form of a complex of 1,3-bis (diphenylphosphino)propane and palladium(II) chloride or acetate.

11. A process according to claim 5, wherein the nickel salt is nickel chloride or nickel acetylacetonate.

12. A process according to claim 5 wherein the nickel salt is added to the reaction mixture with an organophosphorus compound comprising trivalent phosphorus.

13. A process according to claim 5 wherein the nickel salt is in the form of a complex with an organophosphorus compound comprising trivalent phosphorus.

14. A process according to claim 5 wherein the nickel salt is pretreated with a reducing agent.

15. A process according to claim 1 wherein the glycolic diether is dimethoxyethane.

16. A process according to claim 1 wherein the reaction mixture comprises a solvent of the monoether or cyclic mono- or diether type.

17. A process according to claim 16, wherein the solvent of the monoether type is methyl tert-butyl ether or dibutyl ether and the solvent of the cyclic mono- or diether type is tetrahydrofuran or dioxane.

* * * * *